United States Patent [19]

Schoendorfer

[11] Patent Number: 4,851,126
[45] Date of Patent: Jul. 25, 1989

[54] APPARATUS AND METHODS FOR GENERATING PLATELET CONCENTRATE

[75] Inventor: Donald W. Schoendorfer, Santa Ana, Calif.

[73] Assignee: Baxter International Inc., Deerfield, Ill.

[21] Appl. No.: 125,099

[22] Filed: Nov. 25, 1987

[51] Int. Cl.⁴ .................. B01D 13/00; B01D 35/00
[52] U.S. Cl. .................. 210/651; 210/195.2; 210/297; 210/321.67; 210/324; 210/335; 210/782; 210/790; 210/805; 210/806; 604/6
[58] Field of Search .................. 604/4, 5, 6, 406, 410; 210/651, 782, 784, 787, 789, 790, 805, 806, 195.1, 195.2, 297, 322, 321.67, 324, 323.1, 335; 435/2

[56] References Cited

U.S. PATENT DOCUMENTS

| | | | |
|---|---|---|---|
| 3,022,937 | 2/1962 | Dega | 494/65 |
| 3,519,201 | 7/1970 | Eisel et al. | 494/67 |
| 3,655,123 | 4/1972 | Judson et al. | 604/6 |
| 3,955,755 | 5/1976 | Breillatt, Jr. et al. | 494/42 |
| 3,986,506 | 10/1976 | Garber et al. | 604/410 |
| 4,191,182 | 3/1980 | Popovich et al. | 210/651 |
| 4,223,672 | 9/1980 | Terman et al. | 210/782 |
| 4,262,840 | 4/1981 | Gronert et al. | 494/60 |
| 4,341,343 | 7/1982 | Beckman | 494/84 |
| 4,350,156 | 9/1982 | Malchesky et al. | 604/6 |
| 4,464,167 | 8/1984 | Schoendorfer et al. | 604/6 |
| 4,526,515 | 7/1985 | De Vries | 604/6 |
| 4,530,691 | 7/1985 | Brown | 494/45 |
| 4,605,503 | 8/1986 | Bilstad | 604/6 |
| 4,636,193 | 1/1987 | Cullis | 604/6 |
| 4,637,813 | 1/1987 | De Vries | 604/6 |
| 4,680,025 | 7/1987 | Kruger et al. | 604/6 |
| 4,734,089 | 3/1988 | Cullis | 604/6 |
| 4,776,964 | 10/1988 | Schoendorfer et al. | 210/782 |

FOREIGN PATENT DOCUMENTS 8805332 7/1988 World Int. Prop. O.

Primary Examiner—W. Gary Jones
Attorney, Agent, or Firm—Paul C. Flattery; Bradford R. L. Price; Richard G. Besha

[57] ABSTRACT

A tubing or harness set is provided having first and second portions sequentially applicable to a microprocessor-controlled hemapheresis instrument for generating platelet concentrate. The first portion includes a reservoir having dual compartments and a separator. The instrument and the first portion of the harness set alternately collect whole blood from the donor and reinfuse packed cells into the donor while simultaneously continuously separating whole blood into packed cells and platelet-rich plasma. Upon collection of a predetermined quantity of platelet-rich plasma, the donor is disconnected form the phlebotomy needle of the harness, the first harness portion is removed from the instrument and the second harness portion is applied to the instrument. The second harness portion includes a separator for receiving platelet-rich plasma from the collection container of the first harness portion and separating such plasma into platelet concentrate and platelet-depleted plasma.

25 Claims, 3 Drawing Sheets

APPARATUS AND METHODS FOR GENERATING PLATELET CONCENTRATE

BACKGROUND OF THE INVENTION

The present invention relates generally to apparatus and methods for separating constituents of blood and particularly relates to apparatus and methods for generating platelet concentrate from whole blood.

There are a number of automated, on-line donor hemapheresis systems for the separation of whole blood into two or more of its constituents. Such systems are designed to collect a predetermined volume of plasma from a donor using a fully automated processing program in conjunction with a hemapheresis instrument and a disposable tubing set or harness packaged separately from the instrument. In U.S. patent application Ser. No. 644,032, filed Aug. 24, 1984, now U.S. Pat. No. 4,776,964, there is disclosed a two-needle system for the continuous separation of platelet concentrate from whole blood. In that system, whole blood is first separated into platelet-rich plasma and packed cells, the latter being returned to the donor by way of the separate second needle. The platelet-rich plasma is then separated into platelet-poor or depleted plasma and platelet concentrate. While the two separations are performed sequentially, the system is continuous in that platelet concentrate is generated continuously while the system is connected with the donor.

Another automated system for separating blood into components, including platelet-rich plasma, is the CS-300 ® centrifugal separator sold by Baxter Healthcare Corp. of Deerfield, Ill., U.S.A.

There has also been developed an instrument which provides for alternate blood collection and packed cell reinfusion cycles through a single needle, while simultaneously and continuously separating whole blood into packed cells and platelet-rich plasma. Such platelet-rich plasma has a platelet count of approximately 600,000 platelets per microliter. To further concentrate the platelet-rich plasma, it has been the practice to send the container having the platelet-rich plasma to another location, i.e., a laboratory, where another separator is used to separate platelet concentrate from the platelet-poor plasma. The platelet concentrate, following a period of incubation, rest and then resuspension would then be stored until use. Such platelet concentrate has about 1.8 million platelets, or more, per microliter of plasma.

As will be appreciated, there is little world market for platelet-rich plasma directly inasmuch as clinicians do not transfuse platelet-rich plasma directly but do transfuse platelet concentrate.

Thus, platelet concentrate is the more significant product. However, the logistics of the secondary separation of platelet-rich plasma into platelet concentrate is significant inasmuch as generation of platelet-rich plasma from whole blood and concentrating those platelets into platelet concentrate is usually performed by different people, with different objectives. The latter requires a significant amount of attention and talent and there are many aspects of the procedure where error could affect the quality of the results. Thus, it is desirable to generate the platelet concentrate generally at about the time whole blood is taken from the donor and first separated into platelet-rich plasma, and have one person responsible for preparing the concentrate.

According to the present invention, the platelet-rich plasma is concentrated into platelet concentrate and platelet-poor plasma using the same instrument designed for producing platelet-rich plasma immediately following the taking of whole blood from the donor. Additionally, the procedure of the present invention for producing platelet concentrate does not subtract from or add to the critical donor connect time on the instrument as compared with the time on the instrument for producing platelet-rich plasma. That is, when producing platelet-rich plasma, there is usually a time period after the donor is disconnected from the instrument during which the donor rests in the donor chair next to the instrument and the instrument is not used. This time period is used to advantage in the present invention to further process the platelet-rich plasma to platelet concentrate by using the otherwise idle instrument. Consequently, the present invention concentrates platelet-rich plasma into platelet concentrate and platelet-poor or platelet-depleted plasma discontinuously with the initial collection and separation of whole blood into platelet-rich plasma and packed cells and after the donor has been disconnected from the collection and reinfusion harness set. Advantageously, platelet concentrate may be produced in accordance with this invention in conjunction with a novel tube set or harness which enables single-needle alternate collection of whole blood and reinfusion of packed cells while the separator continuously separates platelet-rich plasma from the whole blood.

To accomplish this, the harness set has first and second integrally connected tubing portions, each containing a separator. The first tubing portion contains a reservoir having dual compartments. After the first tubing portion is applied to the instrument and venepuncture is accomplished, collection of platelet-rich plasma is effected by alternately collecting anticoagulated whole blood and reinfusing packed cells. Simultaneously, the instrument and first tubing portion cooperate to continuously separate platelet-rich plasma and packed cells. Once a sufficient quantity of platelet-rich plasma is obtained, the first tubing portion is sealed, severed from the second tubing portion and disconnected from the instrument. The donor is also disconnected from the harness set. Thereafter, the second tubing portion is applied to the instrument for processing the platelet-rich plasma to generate platelet concentrate. It will be appreciated that the foregoing is accomplished in an entirely closed system thereby maintaining system sterility throughout. Moreover, the same operator who performed the venepuncture and obtained the initial separation of anticoagulated whole blood into platelet-rich plasma and packed cells also performs the platelet concentration. The latter may be effected during the time subsequent to blood collection when the donor is resting and the instrument is otherwise idle. Improved quality and control of this quality is thus achieved.

In accordance with a specific preferred embodiment of the present invention, there is provided a method for separating blood into constituents, comprising the steps of providing a first tubing portion having a first blood separator and a phlebotomy needle, applying the first tubing portion to an apheresis instrument, connecting the needle to a blood donor to supply whole blood to the first tubing portion, operating the instrument to flow whole blood to the separator, separating from the whole blood in the first separator a first-blood-constituent-rich plasma, providing a second tubing portion having a second blood separator, disconnecting the phlebotomy needle from the donor, removing the first tubing portion from the instrument, applying the second tubing portion to the instrument, operating the instrument to supply the first-blood-constituent-rich plasma to the second separator and separating the first-blood-constituent from the first-blood-constituent-rich plasma to provide a first-blood-constituent concentrate.

In accordance with another aspect of the present invention, there is also provided a method for separating blood into constituents, comprising the steps of providing a tubing set having first and second blood separators and a phlebotomy needle, applying part of the tubing set including the first separator to an apheresis instrument, connecting the needle to a blood donor, operating the instrument to flow blood from the donor to the first separator, separating from the whole blood in the first separator a first-blood-constituent-rich plasma, thereafter applying another part of the tubing set including the second blood separator to the instrument, operating the instrument to supply the first-blood-constituent-rich plasma to the second separator and separating in the second separator the first-blood-constituent from the first-blood-constituent-rich plasma to provide a first-blood-constituent concentrate.

In a further embodiment of the present invention, there is provided a harness set for application to an apheresis instrument, comprising first and second separators for separating blood into constituent parts, a phlebotomy needle, a first-blood-constituent-rich plasma collection container, first tubing means connected to the phlebotomy needle, the first separator and the container for supplying whole blood from a donor to the first separator for separation into a first-blood-constituent-rich plasma and for supplying the first-blood-constituent-rich plasma to the container, a first-blood-constituent concentrate collection container, second tubing means connected to the first-blood-constituent-rich plasma collection container, the second separator and the concentrate collection container for supplying the first-blood-constituent-rich plasma in the first-blood-constituent-rich plasma collection container to the second separator for separation into a first-blood-constituent concentrate and for supplying the concentrate to the concentrate container.

Accordingly, it is a primary object of the present invention to provide novel and improved apparatus and methods for generating platelet concentrate wherein a single microprocessor controlled hemapheresis instrument is used in conjunction with an integrated harness set having first and second tubing portions sequentially applied to the instrument to first produce platelet-rich plasma from the donor's anticoagulated whole blood and, thereafter generate platelet concentrate from the platelet-rich plasma after the donor has been disconnected from the harness set and instrument.

These and further objects and advantages of the present invention will become more apparent upon reference to the following specification, appended claims and drawings.

BRIEF DESCRIPTION OF THE DRAWING FIGURES

DETAILED DESCRIPTION OF THE DRAWING FIGURES

Reference will now be made in detail to the present preferred embodiment of the invention, an example of which is illustrated in the accompanying drawings.

Figure 1:
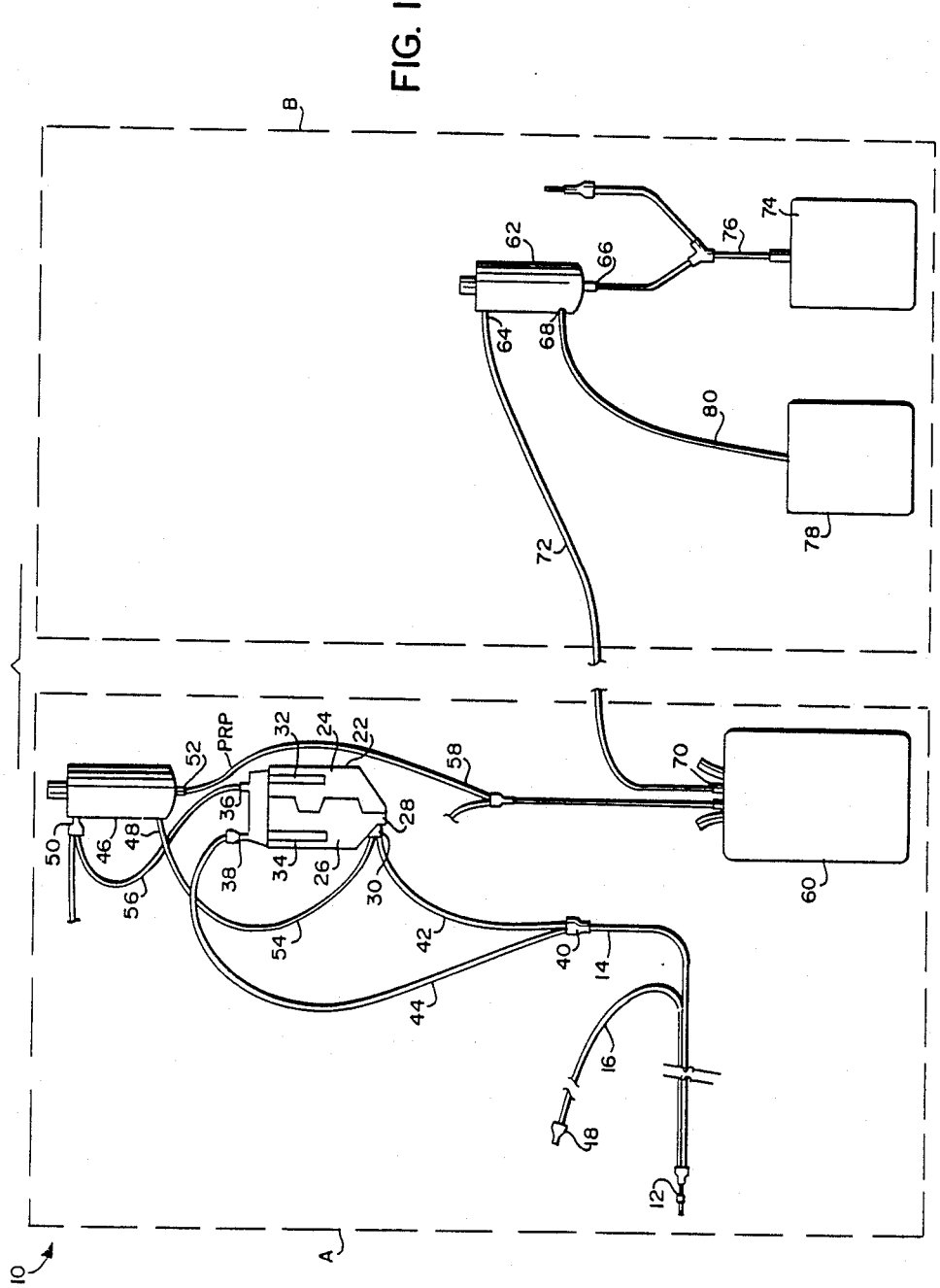
FIG. 1 is a schematic view of a tubing or harness set for use in the generation of platelet concentrate in accordance with the present invention.

Referring now to the drawings, particularly to FIG. 1, there is illustrated a tubing or harness set, generally designated 10. In accordance with the present invention, harness set 10 may be applied to a microprocessor controlled hemapheresis instrument, for example, the instrument H illustrated in FIGS. 2 and 3, in a manner to effect collection of whole blood from a donor through a single needle, separation of the whole blood into packed blood cells and platelet-rich plasma, reinfusion of the packed blood cells to the donor, and subsequent separation of platelets from the platelet-rich plasma to provide platelet concentrate. While the present invention is described in conjunction with a single needle venepuncture set with its attendant features and advantages, it will be appreciated that the invention is also applicable to two-needle systems.

Tubing set 10 is provided with a single venepuncture needle set 12 for alternately receiving whole blood from a donor and reinfusing packed cells into the donor. Venepuncture needle set 12 communicates with a blood line 14. An anticoagulant line 16 has an anticoagulant spike 18 at one end for reception in an anticoagulant supply container 20, illustrated in FIG. 2. At the opposite end, anticoagulant line 16 joins blood line 14 in a Y-connection closely adjacent the single venepuncture needle 12.

Tubing set 10 also includes a reservoir 22. Reservoir 22 is divided into a pair of side-by-side compartments 24 and 26. Outlet ports 28 and 30 are provided at the lower ends of compartments 24 and 26, respectively. Draw tubes 32 and 34 are disposed in compartments 24 and 26, respectively, in communication with respective outlet ports 36 and 38 at the upper end of reservoir 22. Blood line 14 branches, at a Y-connection 40, into branch line 42 connecting blood line 14 with inlet port 28 of compartment 24, and a branch line 44 which connects blood line 14 with outlet port 38 of compartment 26. Tubing set 10 additionally includes a separator 46 for separating platelet-rich plasma and packed cells from anticoagulated whole blood. A separator of this type is described and illustrated in co-pending U.S. patent application Serial No. 002,804, entitled "Continuous Centrifugation System and Method for Directly Deriving Intermediate Density Material from a Suspension." Suffice to say for present purposes, separator 46 has a whole blood inlet port 48, a packed cell outlet port 50 and a platelet-rich plasma outlet port 52. Line 54 connects the lower whole blood outlet port 30 of reservoir compartment 26 with the inlet port 48 of separator 46. Line 56 connects the packed cell outlet port 50 of separator 46 with inlet port 36 for supplying packed cells to compartment 24 of reservoir 22. Tubing 58 connects between the platelet-rich plasma outlet port 52 of separator 46 and a platelet-rich plasma collection container 60.

The foregoing described portion of harness set 10 is, for convenience hereafter, identified as the first tubing portion, whereas the following description of the remaining portions of tubing or harness set 10 is identified as the second tubing portion. It will be appreciated from this description that the first and second tubing portions form an integral or unitary harness set 10 which is packaged and sold for one-time use with the instrument H disclosed in FIGS. 2 and 3 hereof.

The second tubing portion of harness set 10 also includes in use the platelet-rich plasma container 60 which serves as the platelet-rich plasma supply from which platelets are concentrated upon application of the second tubing portion to instrument H, as described hereinafter. The second tubing portion also includes a separator 62 of the rotary filter membrane type. Suffice to say, this separation chamber 62 filters the platelet-rich plasma received from container 60 to provide platelet concentrate and platelet-poor or depleted plasma filtrate. Separator 62 has a platelet-rich plasma inlet port 64, a platelet-poor or depleted plasma outlet port 66 and a platelet concentrate outlet port 68. Container 60 has a platelet-rich plasma outlet port 70 in communication with inlet port 64 of separator 62 via tubing 72. A platelet-poor plasma collection container 74 communicates with the outlet port 66 of separator 62 via tubing 76. Finally, platelet concentrate outlet port 68 of separator 62 communicates with a platelet concentrate collection container 78 via tubing 80.

As an alternative, the platelet-rich plasma tubing 72 may be connected to the lower tangential port 68 of separator 62 and the platelet concentrate tubing 80 may be connected to the upper tangential port 64 of separator 62. The separator will operate to provide platelet concentrate using this alternate connection. However, the illustrated embodiment is preferred because it facilitates ready removal of the final aliquot of blood product from separator 62 at the end of the procedure.

As indicated previously, harness set 10 is disposable and preferably each of the first and second tubing portions are separately provided in discrete flexible plastic containers or pouches indicated by the dashed lines designated A and B, respectively, in FIG. 1. Thus, when the first tubing portion is used in conjunction with the instrument illustrated in FIGS. 2 and 3, as hereinafter described, the second tubing portion may be retained in its plastic container or pouch B and disposed on an available hook on the instrument until the first tubing portion is removed from the instrument and the second tubing portion is applied thereto. It will be understood, however, that the first and second tubing portions are integrally connected one to the other and comprise a single closed blood collection, reinfusing and separation system. Accordingly, while the first and second tubing portions may be provided in discrete pouches A and B, they are interconnected and their provision in discrete pouches is for convenience of use only as will be apparent from this description.

Figure 2:
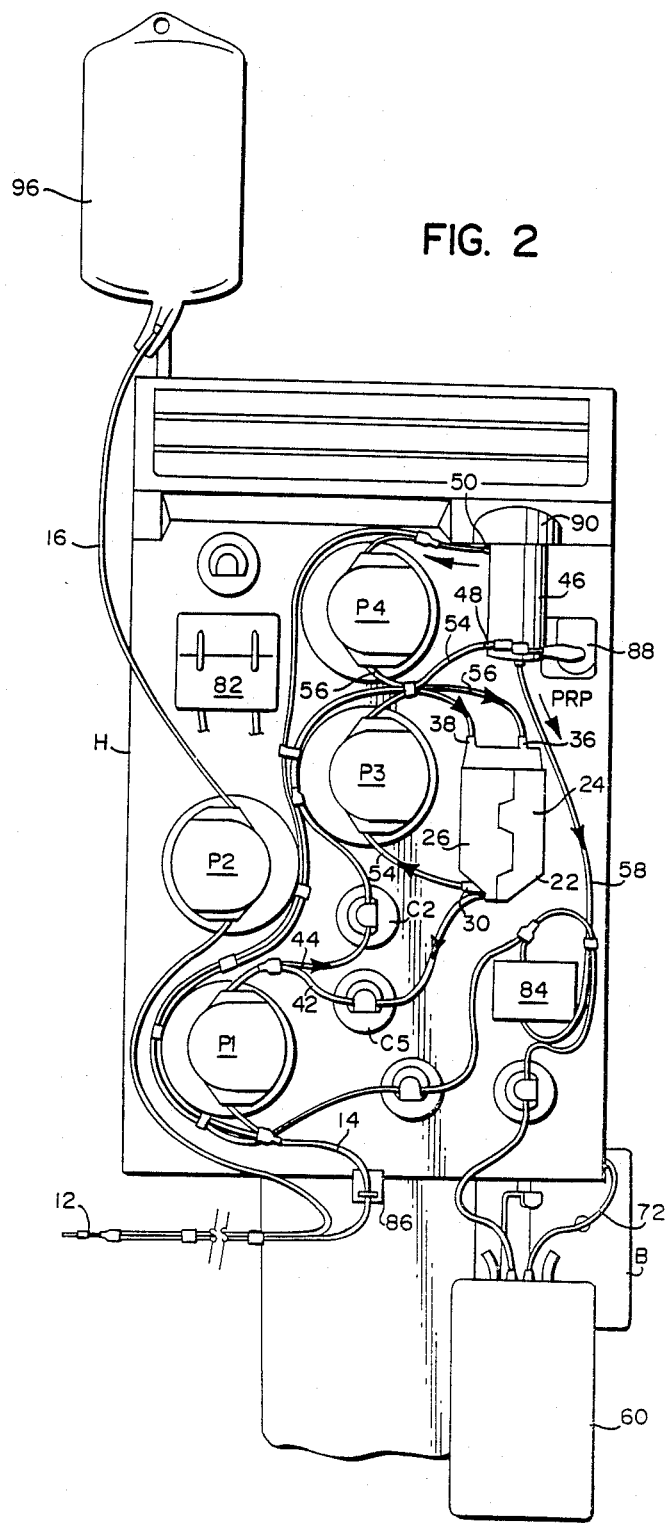
FIG. 2 is a front elevational view of a hemapheresis instrument illustrating a first tubing portion of the harness set of FIG. 1 applied to the instrument.
Figure 3:
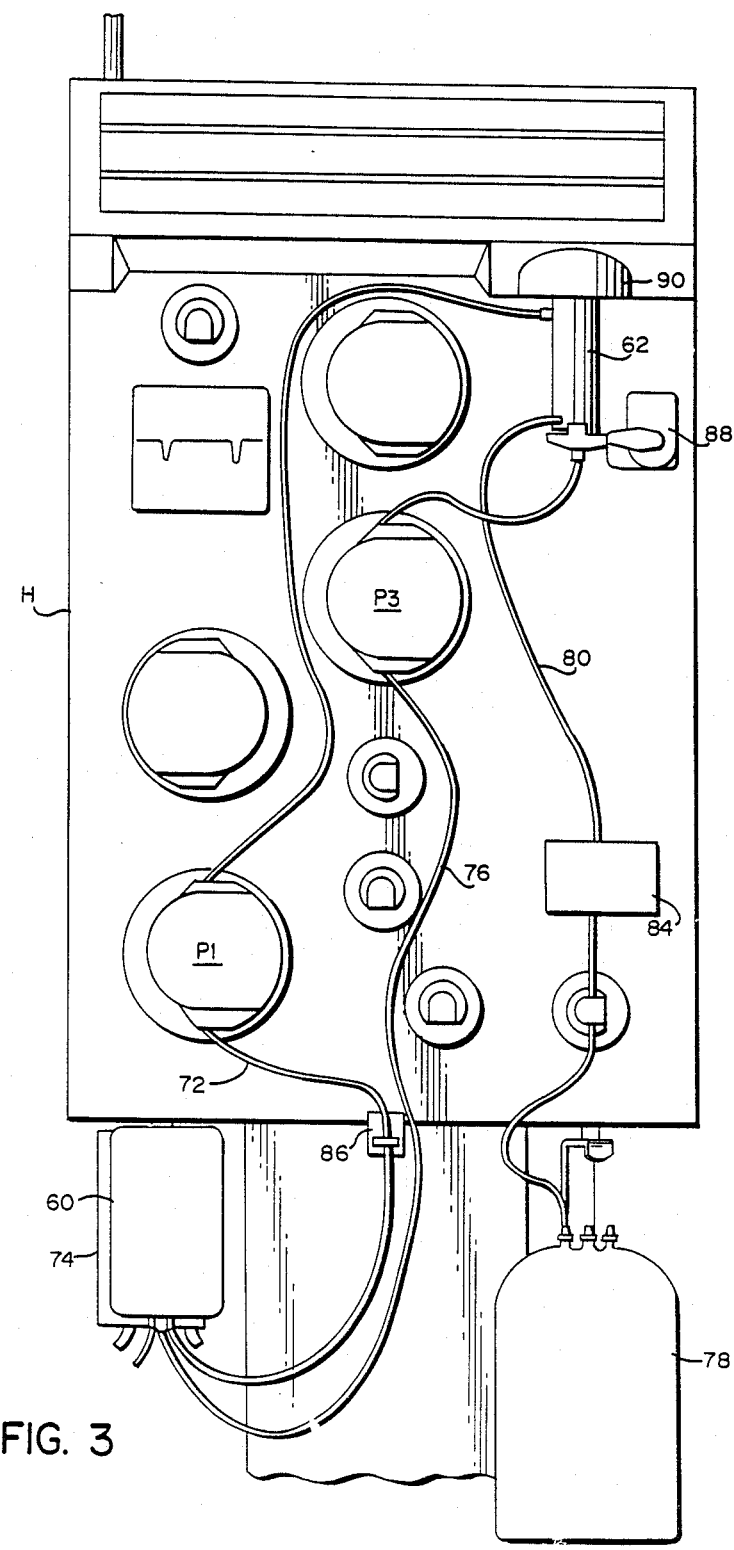
FIG. 3 is a view similar to FIG. 2 illustrating the hemapheresis instrument with a second tubing portion of the harness set applied to the instrument.

Turning now to FIGS. 2 and 3, the relevant operating components of the hemapheresis instrument H will now be described. The instrument is provided with various pumps, detectors, clamps, and the like, under control of a microprocessor, for cooperation with harness set 10 when applied to the instrument. As illustrated in FIG. 2, and in relevant part, there are provided pumps P1, P2, P3 and P4 on the front face of instrument H. These pumps are preferably of the peristaltic type and cooperate with the various tubings of the harness set to flow blood in the desired directions between the various elements of the harness set. Also, a series of clamps are provided which receive various tubings of harness set 10. The clamps are movable between open or closed positions and thus operate to open or close the tubings disposed in the clamps. For present purposes, only clamps C2 and C5 need be identified. The face of the instrument also contains a pressure transducer 82, a hemoglobin detector 84, an air detector 86, sensors, not shown, for determining the levels of liquid in reservoir 22, and a mount or lower holder 88 for the separators 46 and 62 of harness set 10. The face of instrument H also includes a motor cup 90 for mounting motor magnets which, in turn, drive the separator rotors. Thus, separators 46 and 62 may be installed sequentially on lower mount 88 with their upper ends in the motor cup, whereby magnetic connection is effected between the magnetic drive motor and the rotor of the installed separator.

In accordance with the method of separating blood into constituent parts according to the present invention, the first tubing portion of harness set 10 is applied to the instrument face, while the second tubing portion is preferably retained in its pouch B and hung from an available hook on the instrument. Under control of the microprocessor, instrument H operates the pumps, clamps, detectors and the like in conjunction with the first tubing portion of harness set 10 to separate platelet-rich plasma from whole blood and reinfuse packed cells into the donor. The first tubing portion 10 is then removed from the instrument, severed from the second tubing portion and discarded. The donor is also disconnected from the harness set and the instrument. The second tubing portion is then applied to the instrument to generate platelet concentrate from the platelet-rich plasma previously generated. The procedure for ultimately providing platelet concentrate will now be described in detail.

The various tubings of the first tubing portion are applied to instrument H as follows: blood line 14 is disposed in blood pump P1; lines 42 and 44 are disposed in clamps C5 and C2, respectively; line 54 is applied to pump P3 and line 56 is applied to pump P4. Reservoir 22 is mounted on the face of the instrument, by means not shown, and separator 46 is disposed on mount 88 with its upper end disposed in motor cup 90 such that the drive rotor of separator 46 is coupled magnetically to the drive motor of the instrument. Platelet-rich plasma line 58 is disposed in hemoglobin detector 84 and platelet-rich plasma container 60 is hung from a weight scale on a lower part of the instrument. Anticoagulant line 16 is connected at one end to a supply of anticoagulant, i.e., supply container 96, for supplying anticoagulant via line 16 to blood line 14 adjacent the venepuncture needle 12. The blood line 14 is also passed through air detector 86. The second tubing portion is retained in its individual pouch B which is hung from an available hook on the instrument in an out-of-the-way location.

In operation, various procedures are followed under control of the microprocessor for performing certain instrument functions which need not be described herein. Suffice to say, that after set-up and following venepuncture performed on the donor and priming of the separator and reservoir, the instrument, in conjunction with the first tubing portion, is ready to alternately collect whole blood from the donor and reinfuse packed red cells into the donor while whole blood is simultaneously and continuously supplied to the separation device to produce platelet-rich plasma and packed cells. Thus, clamp C2 is opened, clamp C5 is closed and pumps P1, P2, P3 and P4 are actuated. Whole blood therefore flows through the single venepuncture needle 12 and blood line 14, past open clamp C2, and into whole blood compartment 26 via branch line 44 and inlet port 38 of reservoir 22. Anticoagulant is added to the whole blood by pump P2 via line 16 at its Y-connection with blood line 14. Closed clamp C5 prevents flow of anticoagulated whole blood into reinfusion line 42. Pump P3 pumps whole blood from compartment 26 through outlet port 30 via line 54 into separator 46 via inlet port 48. Packed cells are pumped from separator 46 through outlet 50 via line 56 by pump P4 into reservoir compartment 24 through inlet port 36. Platelet-rich plasma flows from separator 46 via line 58 into collection container 60. Thus, during collection, anticoagulated whole blood is supplied compartment 26 and separator 46 while packed cells are supplied compartment 24 and platelet-rich plasma is supplied container 60.

The system hereof provides for the alternate collection of whole blood from the donor and reinfusion of packed cells or platelet-depleted plasma into the donor while separator 46 simultaneously and continuously receives anticoagulated whole blood for separation into the platelet-rich plasma and packed cells. To accomplish this, sensors, not shown, on the instrument face detect the level of fluids in the compartments of the reservoir. When the compartments are full, the microprocessor, in response to the detected signals, causes instrument H to change from its blood collection cycle to its reinfusion cycle. In the reinfusion cycle, clamp C2 is closed and clamp C5 is opened, pump P2 is stopped, and pump P1 is reversed to pump packed cells from compartment 24 of reservoir 22 into the donor through venepuncture needle 12. Pumps P3 and P4, however, continue to operate to respectively provide anticoagulated whole blood from the compartment 26 of reservoir 22 to separator 46 and supply packed cells from separator 46 to compartment 24 of reservoir 22. When the packed cells and the supply of whole blood are substantially depleted from compartments 24 and 26, respectively, these low liquid levels are sensed. At that time, the microprocessor causes instrument H to change from its reinfusion cycle to its blood collection cycle. Thus, clamp C2 is opened, clamp C5 is closed, pump P2 is started, and pump P1 is reversed to again flow anticoagulated whole blood to the whole blood compartment 26, which has been substantially depleted of whole blood during the reinfusion cycle. It will be appreciated that during the alternate collection and reinfusion cycles, whole blood is continuously pumped from reservoir compartment 26 to separator 46 by pump P3 whereby separation is effected continuously. Thus, platelet-rich plasma flows continuously from separator 46, while anticoagulated whole blood is continuously supplying separator 46. When the desired quantity of platelet-rich plasma has been collected in container 60, the microprocessor controls the instrument to purge the system of blood products. At this time, it will be appreciated that the venepuncture needle 12 is withdrawn from the donor and the donor is otherwise disconnected from instrument H.

Having collected the desired quantity of platelet-rich plasma in collection container 60, the first tubing portion of harness set 10 is removed from the instrument. The platelet-rich plasma line 58 is then heat-sealed just above the inlet port to container 60. The first tubing portion may then be cut away above the seal and discarded. The second tubing portion, including container 60 with the platelet-rich plasma therein, is then applied to instrument H, as illustrated in FIG. 3. It will be appreciated that in the preferred embodiment, the same instrument H is used, although it will be recognized that this separate operation to produce the platelet concentrate may be performed on a separate instrument. To accomplish this, container 60, the platelet-poor plasma bag 74 and the platelet concentrate container 78 are hung from hooks conveniently disposed along the underside of the instrument. Separator 62 is disposed on mounting 88 and its upper end is disposed in mounting cup 90 for magnetic coupling with the drive motor of the instrument. Tubing 72 interconnecting platelet-rich plasma container 60 and separator 62 is disposed in pump P1 and the ultrasonic air detector 86. Tubing 76 is disposed about pump P3, while tubing 80 is disposed in the hemoglobin detector 84.

To produce platelet concentrate, the microprocessor controls the instrument to actuate pump P1 to pump platelet-rich plasma from container 60 into separator 62. The rotary membrane filter of separator 62 causes the platelet-rich plasma to separate into platelet-poor plasma and platelet concentrate. The platelet-poor plasma is pumped by pump P3 from separator 62 for flow via line 76 for collection in container 74. The desired platelet concentrate flows from separator 62 via line 80 through the hemoglobin detector 84 into platelet concentrate container 78.

The instrument is programmed such that it knows the weight of the platelet-rich plasma collected in the first cycle. Additionally, the phlebotomist has input the instrument with the desired quantity of platelet concentrate. The pumps are controlled by the microprocessor such that the desired quantity of product is provided platelet concentrate collection container 78. At the end of the procedure, the platelet-rich plasma bag is sensed for air in the tube 72 in ultrasonic air detector 86, indicating the end of the platelet concentration cycle. If the final weight of platelet concentrate is low, the instrument can pump platelet-poor plasma back through the device and into the platelet concentrate bag. If the final weight of the platelet concentrate is high, the instrument can pump more platelet concentrate back through separator 62 into the platelet-rich plasma container and reprocess.

Significantly, the platelets separated by separation device 62 require no incubation period or resuspension procedure to produce infusable platelets. This greatly reduces labor and improves the quality of the product.

Consequently, it will be appreciated that, in accordance with the present invention, there has been provided apparatus and methods for producing platelet concentrate from platelet-rich plasma in a discontinuous process after the donor is disconnected from the harness set. The instrument retains all of the advantages of alternating collection and reinfusion cycles with continuous flow of whole blood through the first separator for continuous separation, with the additional advantage that the platelet concentration procedure may take place immediately subsequent to the platelet-rich plasma collection procedure on the same instrument while the donor is disconnected from the harness set and instrument and is at rest. Platelet concentration is achieved without effectively increasing instrument or donor time because both donor and the instrument would normally be at rest immediately subsequent to the platelet-rich plasma collection procedure.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for separating blood into constituents, comprising the steps of:
   providing a first tubing portion having a first blood separator and a phlebotomy needle;
   applying said first tubing portion to an apheresis instrument;
   connecting the needle to a blood donor to supply whole blood to the first tubing portion;
   operating the instrument to flow whole blood to the separator;
   separating from the whole blood in the first separator a first-blood-constituent-rich plasma;
   providing a second tubing portion having a second blood separator;
   disconnecting the phlebotomy needle from the donor;
   removing the first tubing portion from the instrument;
   applying the second tubing portion to the instrument;
   operating the instrument to supply the first-blood-constituent-rich plasma to the second separator; and
   separating the first-blood-constituent from the first-blood-constituent-rich plasma to provide a first-blood-constituent concentrate.

2. A method according to claim 1 including providing first and second tubing portions integral one with the other as part of a unitary tubing set.

3. A method according to claim 1 wherein said instrument has a pump, the step of applying the first tubing portion to the instrument including applying a tube thereof to the pump for pumping whole blood to the first separator, and wherein the step of applying the second tubing portion to the instrument includes applying a tube thereof to the pump for pumping the first-blood-constituent-rich plasma to the second separator.

4. A method according to claim 1 wherein each of said separators has a rotary element to facilitate the respective separation, said instrument having at least one drive means for driving said elements, wherein the step of applying the first and second tubing portions to the instrument includes applying the first and second separators thereof sequentially to the same drive means such that the rotatable element of each separator is driven by the same drive means.

5. A method according to claim 1 including providing said first and second tubing portions integral one with the other as part of a unitary tubing set, providing a container for receiving the first-blood-constituent-rich plasma from the first separator and sealing the container from the first tubing portion after the first-blood-constituent-rich plasma has been separated, and before the instrument is operated to provide the first-blood-constituent-rich plasma to the second separator.

6. A method according to claim 5 including, after sealing, severing the first tubing portion from the second tubing portion.

7. A method according to claim 5 wherein the first and second tubing portions constitute a closed system for retaining the blood constituents, and including the further steps of separating the first tubing portion from the second tubing portion after sealing the container such that the separated blood constituents remain in a closed system.

8. A method according to claim 1 wherein each of said separators has a rotary element to facilitate the respective separation, said instrument having a pump and a single means for driving said elements, the step of applying the first tubing portion to the instrument including applying a tubing thereof to the pump for pumping whole blood to said first separator, the step of applying the second tubing portion to the instrument including applying a tubing thereof to the pump for pumping the first-blood-constituent-rich plasma to the second separator, the step of applying the first and second tubing portions to the instrument including applying the separators thereof sequentially to the single drive means such that each separator is driven by the same drive means.

9. A method according to claim 8 including providing said first and second tubing portions integral one with the other as part of a unitary tubing set, providing a container for receiving the first-blood-constituent-rich plasma from the first separator, and sealing the container from the first tubing portion after the first-blood-constituent-rich plasma has been separated, and before the instrument is operated to provide the first-blood-constituent-rich plasma to the second separator, said first and second tubing portions constituting a closed system for retaining the blood constituents, and including separating the first tubing portion from the second tubing portion after sealing the container such that the separated blood constituents remain in a closed system.

10. A method according to claim 1 including continuously separating the first-blood-constituent-rich plasma while alternating collecting whole blood from the donor and reinfusing first-blood-constituent-depleted plasma into the donor.

11. A method according to claim 1 including separating packed cells from the whole blood in the first separator, and wherein the first tubing portion includes a reservoir for receiving the packed cells from the first separator and whole blood from the donor and further including the step of alternately collecting whole blood from the donor in said reservoir and reinfusing the packed cells from the reservoir into the donor while simultaneously and continuously separating the first-blood-constituent-rich plasma from the whole blood in the first separator.

12. A method according to claim 1 wherein the first and second tubing portions are applied to the same instrument.

13. A method for separating blood into constituents, comprising the steps of:
   providing a tubing set having first and second blood separators and a phlebotomy needle;
   applying part of said tubing set including the first separator to an apheresis instrument;
   connecting the needle to a blood donor;
   operating the instrument to flow blood from the donor to the first separator;
   separating from the whole blood in the first separator a first-blood-constituent-rich plasma;
   thereafter applying another part of said tubing set including the second blood separator to the instrument;
   operating the instrument to supply the first-blood-constituent-rich plasma to the second separator; and separating in the second separator the first-blood-constituent from the first-blood-constituent-rich plasma to provide a first-blood-constituent concentrate.

14. A method according to claim 13 including disconnecting the needle from the donor after the first-blood-constituent-rich plasma has been separated and before the first-blood-constituent is separated in the second separator to provide the first-blood-constituent concentrate.

15. A method according to claim 13 including separating packed cells from the whole blood in the first separator and reinfusing into the blood donor through said needle the packed cells separated from the whole blood in the first separator.

16. A method according to claim 13 including continuously separating the first-blood-constituent-rich plasma while alternating collecting whole blood from the donor and reinfusing first-blood-constituent-depleted plasma into the donor.

17. A method according to claim 13 wherein said instrument has a pump, the step of applying the tubing set including the first separator to the instrument including applying a tube thereof to the pump for pumping whole blood to the first separator and wherein the step of applying the tubing set includes the second separator to the instrument includes applying a tube thereof to the pump for pumping the first-blood-constituent-rich plasma to the second separator.

18. A method according to claim 13 wherein each of said separators has a rotary element to facilitate the respective separation, said instrument having a single means for driving said elements, wherein the step of applying the tubing set to the instrument includes applying the first and second separators thereof sequentially to the single drive means such that the rotatable element of each separator is driven by the same drive means.

19. A method according to claim 13 including providing a container for receiving the first-blood-constituent-rich plasma from the first separator and sealing the container from the first separator after the first-blood-constituent-rich plasma has been separated, and before the instrument is operated to provide the first-blood-constituent-rich plasma to the second separator.

20. A method according to claim 13 including separating packed cells from the whole blood in the first separator, and wherein the part of the tubing set including the first separator also includes a reservoir for receiving the packed cells from the first separator and whole blood from the donor and further including the step of alternately collecting whole blood from the donor in said reservoir and reinfusing the packed cells from the reservoir into the donor, while simultaneously and continuously separating the first-blood-constituent-rich plasma from the whole blood in the first separator.

21. A method according to claim 13 wherein the first-blood-constituent-rich plasma constitutes platelet-rich plasma and the first-blood-constituent concentrate constitutes platelet concentrate.

22. A harness set for application to a blood donor and an apheresis instrument for generating platelet concentrate from the donor's whole blood, comprising:

first and second separators for separating whole blood into platelet-rich plasma and packed cells;
a phlebotomy needle;
a discrete platelet-rich plasma collection container;
first tubing means connected to said phlebotomy needle, said first separator and said container for supplying whole blood from a donor to said first separator for separation into platelet-rich plasma and for supplying the platelet-rich plasma to said container;
a reservoir connected by said first tubing means between said needle and said first separator whereby said first tubing means enables delivery of whole blood from the donor to said reservoir and from said reservoir to said first separator, third tubing means connecting between said first separator and said reservoir for receiving packed cells from said first separator, means for reinfusing the packed cells from said reservoir to the donor through said needle;
a discrete platelet concentrate collection container;
second tubing means connected to said platelet-rich plasma collection container, said second separator and said platelet concentrate collection container for supplying the platelet-rich plasma in said platelet-rich plasma collection container to said second separator for separation into platelet concentrate and for supplying the concentrate to said concentrate container.

23. A harness set according to claim 22 including a reservoir connected by said first tubing means between said needle and said first separator whereby said first tubing means enables delivery of whole blood from the donor to said reservoir and from said reservoir to said first separator, third tubing means connecting between said first separator and said reservoir for receiving a second-blood-constituent from said first separator.

24. A harness set according to claim 23 wherein said reservoir has first and second compartments for receiving whole blood from the donor and packed cells from the first separator, respectively.

25. A harness set according to claim 22 including a collection container for receiving a platelet-poor plasma, said second tubing, means connecting between said second separator and said platelet-poor plasma collection container for supplying the platelet-poor plasma from said second separator to said platelet-poor plasma collection container.

* * * * *